United States Patent
Cracknell

[11] Patent Number: 5,351,521
[45] Date of Patent: Oct. 4, 1994

[54] MEASUREMENT OF GAS AND WATER CONTENT IN OIL

[75] Inventor: David J. Cracknell, Chelmsford, United Kingdom

[73] Assignee: GEC-Marconi Limited, Middlesex, United Kingdom

[21] Appl. No.: 961,167

[22] Filed: Oct. 16, 1992

[30] Foreign Application Priority Data

Oct. 18, 1991 [GB] United Kingdom ............. 9122210.9

[51] Int. Cl.$^5$ ............................................. G01N 22/00
[52] U.S. Cl. ................................. 73/19.1; 73/61.44; 73/86.04; 324/640
[58] Field of Search ............. 73/61.48, 861.04, 61.41, 73/61.43, 61.44, 19.1; 324/637, 640, 639

[56] References Cited

U.S. PATENT DOCUMENTS

| | | | |
|---|---|---|---|
| 3,498,112 | 4/1968 | Howard et al. | 73/61.48 |
| 4,423,623 | 1/1984 | Ho et al. | 73/61.41 |
| 4,429,273 | 1/1984 | Mazzagatti | 324/61 R |
| 4,764,718 | 8/1988 | Revus et al. | 324/637 |
| 4,812,739 | 3/1989 | Swanson | 324/640 |
| 4,820,970 | 4/1989 | Swanson | 324/640 |
| 4,888,547 | 12/1989 | McGinn et al. | 73/61.48 |
| 5,049,823 | 9/1991 | Castel et al. | 73/861.04 |
| 5,103,181 | 4/1992 | Gaisford et al. | 324/637 |
| 5,140,271 | 8/1992 | Marrelli | 73/61.63 |

FOREIGN PATENT DOCUMENTS 0268399  5/1988  European Pat. Off. .
2110377  6/1983  United Kingdom .

*Primary Examiner*—Hezron E. Williams
*Assistant Examiner*—Michael Brock
*Attorney, Agent, or Firm*—Spencer, Frank & Schneider

[57] ABSTRACT

A device for measuring the relative proportions of gas, oil and water in a conductive pipe includes at least one open-ended, conductive tube having a radius different from the pipe, disposed within the pipe. Microwave transmission structure transmits microwave signals along the pipe and the at least one tube at a plurality of frequencies, the pipe and the at least one conductive tube acting as waveguides for the microwave signals. At least two microwave receiving devices are disposed at separate positions having different respective radii, spaced apart along the pipe and at least one tube, for receiving the microwave signals transmitted by the transmission structure. Determining circuitry determines the relative proportions of gas, water and oil in the pipe by comparing the transmitted and received signals.

6 Claims, 2 Drawing Sheets

MEASUREMENT OF GAS AND WATER CONTENT IN OIL

BACKGROUND OF THE INVENTION

This invention relates to the measurement of the gas and water content in oil, particularly crude oil.

Where crude oil is being pumped from the ground it is generally desirable to be able to measure its gas and water content.

In the past a number of methods of measuring the gas and water content of crude oil have been proposed. These generally fall into two groups, the first being methods where a sample of the oil flow is taken and the sample is analysed and the other being so called full flow systems where the aggregate gas and water content of the entire flow is measured.

In general measurements involving sampling have been unpopular because the gas and water content of the oil flow is non-homogenous over time or across the width of a pipe so there is no guarantee that a sample is representative unless a homogenizer is used to homogenize the gas, oil and water in the flow. Generally speaking homogenizers are not completely effective and require power to operate them. The need for such power supply can be a considerable problem in under sea applications but the main problem with systems of this type is the difficulty of ensuring that a sample is fully representative of the gas and water content of the oil flow as a whole, even when a homogenizer is used.

As a result, full flow systems are preferred. One method of carrying out full flow measurement which has been proposed is the use of microwave energy. If microwave energy is passed through a mixture of water, oil and gas it is possible to deduce the proportions of the flow made up of the three constituents by measuring the attenuation of the microwave energy. This is possible because oil, water and gas have very different permitivities.

Theoretically, such a calculation would be extremely simple if the flow of oil, gas and water was homogeneous. However, as explained above, it generally is not homogeneous, and as a result, in practice, it has proved extremely difficult to relate the changes in permitivity measured by microwave absorption systems to the actual proportions of water and gas in the oil flow.

SUMMARY OF THE INVENTION

This invention was intended to produce a method of measurement of the gas and water content in oil overcoming these problems, at least in part.

This invention provides apparatus for measuring the gas and water content in oil flowing along a conductive pipe comprising microwave transmission means able to project microwave energy along the pipe at two frequencies, microwave receiving means able to receive the microwave energy after passing along the pipe, and calculating means arranged to calculate the relative proportions of gas, water and oil in the pipe by comparing the transmitted and received signals, the pipe acting as a waveguide.

The invention is based on the propagation properties of microwaves and RF radiation along circular waveguides. A microwave or RF signal traveling along a tubular waveguide of circular cross section and having conductive walls will travel in one or more of the well known propagating modes, examples of such modes being $TE_{11}$, $TM_{01}$, $T_{21}$ and $TE_{01}$. Each of these modes has a frequency below which it will not propagate along the tube, this frequency is known as both the cut-on and cut-off frequency by different people, but regardless of the terminology used it is the lowest frequency which will propagate along the waveguide in that mode, and it will be referred to herein as the cut-off frequency. The cut-off frequency of a circular tubular waveguide is inversely related to the internal radius of the waveguide and the square root of the dielectric constant of the material filling the waveguide. Thus, the larger the radius of the waveguide, the lower the cut-off frequency will be, and the higher the dielectric constant of the material filling the waveguide, the lower the cut-off frequency will be.

The relationship between cut-off frequency, dielectric constant and radius are well known, for example the mode of the lowest cut-off frequency in a circular waveguide is the $TE_{11}$ or transverse electric mode, the cut-off frequency of which corresponds to the wavelength given by:

$$\lambda_c = 3.412\, R\, \sqrt{\epsilon_r}$$

Where R is the radius of the waveguide and $\sqrt{\epsilon_R}$, is the dielectric constant of the material filling the waveguide.

BRIEF DESCRIPTION OF THE DRAWINGS

Apparatus employing the invention will now be described by way of example only with reference to the accompanying figures in which.

DETAILED DESCRIPTION OF THE PREFERRED EMBODIMENTS

Figure 1:
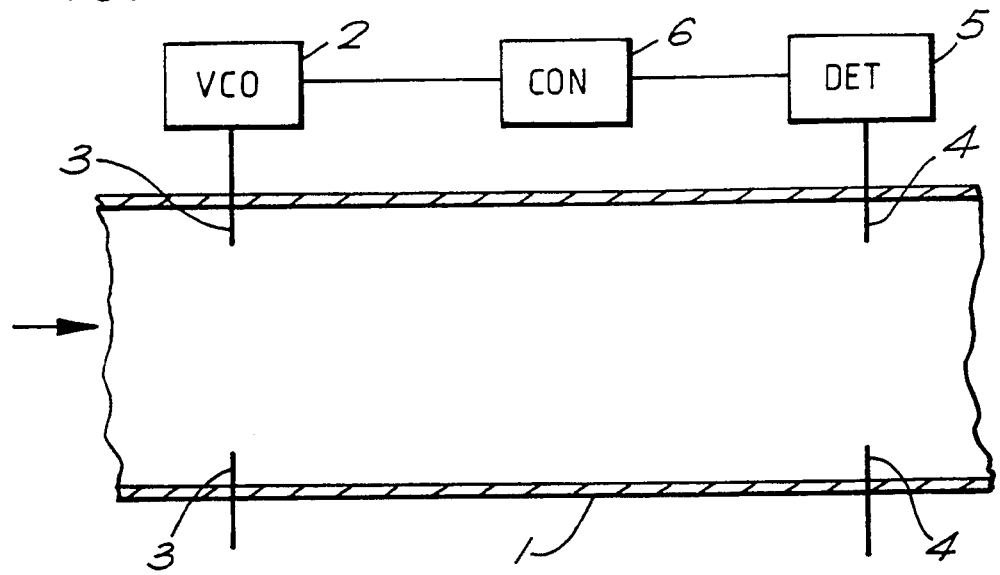
FIG. 1 shows a first system for measuring the relative proportions of oil, water and gas in a fluid flow.

Referring to FIG. 1, a system for finding the dielectric constant of material within a tube is shown. This comprises a voltage controlled oscillator (VCO) 2 built to generate a variable frequency RF (500 MHz to 1 GHz) or microwave (1 GHz to 20 GHz) electromagnetic signal. This signal is supplied to electrodes 3 which launch it in the $TE_{11}$ mode along the tube 1. Further along the tube 1, which is circular and conductive and which acts as a waveguide, is a second pair of electrodes 4 which pick up the signal which is propagated along the pipe 1. The signal received by the electrodes 4 is measured by a detector 5 which supplies them to a controller 6.

In operation, the controller 6 sweeps the voltage generated by the VCO 2 across a range of frequencies from the bottom of the range of the VCO 2 upwards, until a sudden increase in the signal received by the detector 5 shows that the cut-off frequency has been reached and the signal is propagating along the pipe 1. Once the controller 6 knows the cut-off frequency, the dielectric constant of the material within the pipe can easily be calculated because the radius of pipe 1 is known.

It is necessary to look for an increase in the signal sensed by the detector 5 rather than simply looking for any signal at all. This is because even when the signal has too low a frequency to propagate along the waveguide, there will still be some transmission of the signals along the waveguide. This sub cut-off frequency signal will decay expotentially in energy with distance whereas the above cut-off frequency signal will decay in energy due only to absorption due to the loss in the material in the waveguide and the conductivity of the waveguide walls. As a result, it is very easy to tell the difference between the signals received at the second set of electrodes above and below the cut off frequency.

If the contents of the pipe 1 is crude oil, a mixture of oil, water and gas, three different fluids having different dielectric constants, it is not possible to deduce the relative proportions of the fluids without ambiguity from the average dielectric constant of the material within the pipe 1 alone. As a result, a system as simple as this cannot be used to calculate the relative quantities of oil, water and gas in a pipeline.

By comparing the transmitted and received signals at a range of frequencies above the cut off frequency, the insertion loss, insertion phase, and time delay characteristics of the mixture of fluids within the pipe can be found.

Since the complex permitivities, that is, the dielectric constant and absorption coefficient of oil, water and gas, and their dependence on frequency, are all known, the proportions of oil, water and gas within the pipe 1 can be calculated from this information.

Water has both a dielectric constant and absorption coefficient strongly dependent on frequency. At low frequencies the relative dielectric constant of water is approximately 80, falling to less than 30 at 24 Ghz. Over a similar frequency band the absorption coefficient increases from less than 0.1 to 1.0 at 24 GHz. The properties of oil and gas are substantially invariant with frequency. The relative dielectric constant of oil is approximately 2.5 while its absorption coefficient is 0.001. The properties of gas are virtually indistinguishable from those of air.

Figure 2:
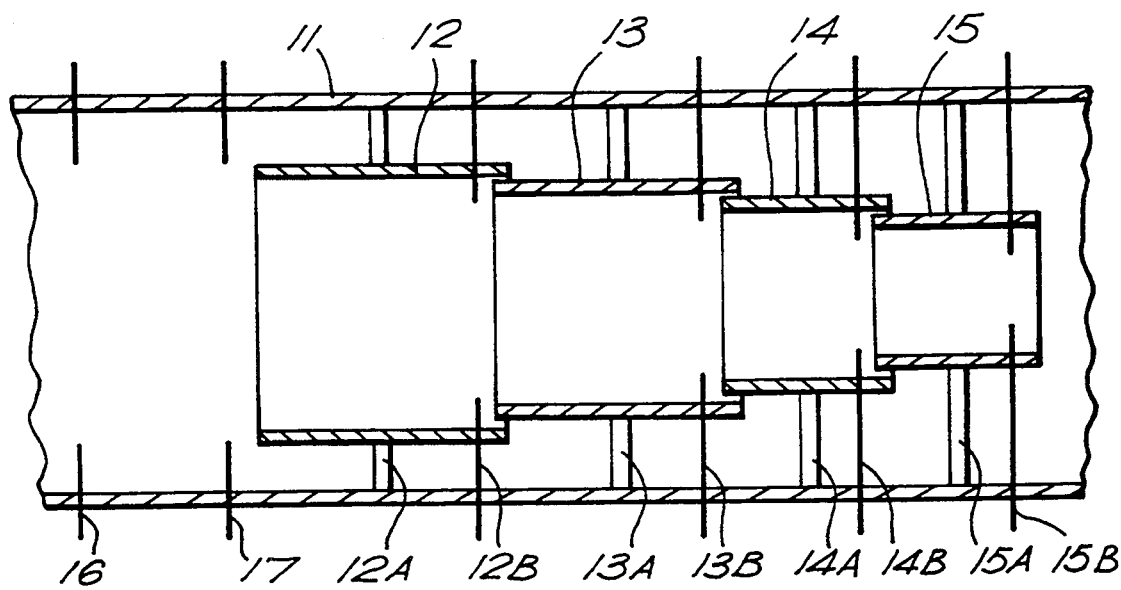
FIG. 2 shows a second system for measuring the relative proportion of oil, water and gas in a fluid flow.

Referring to FIG. 2 a more practical system is shown comprising a conductive pipe 11 containing a plurality of smaller concentric pipes 12, 13, 14 and 15 all having different radii, the pipe 11 and all of the tubes 12 to 15 are conductive and circular in cross section. Each of the tubes 12 to 15 is supported from the wall of the pipe 11 by a respective set of vanes 12a to 15a. Each set of vanes 12a to 15a comprises six vanes equally spaced around the circumference of their respective tubes 12 to 15. A first set of transmission electrodes 16 arranged to transmit an applied electromagnetic signal down the pipe 11 in the TE$_{11}$ mode, and the tube 12 to 15 are arranged along the pipe in order of decreasing radius away from the electrodes 16. Thus, the largest radius tube 12 is nearest to the transmission electrodes 16, with the tube 13 with the next largest radius being placed next furthest from the transmission electrode 16, and so on, until the tube 15 with the smallest radius is arranged furthest from the transmission electrodes 16. Each of tubes 13 to 15 is arranged so that it projects slightly into the tube of next highest radius so that the two tubes overlap for a short distance. The tube of largest radius 12 inevitably overlaps completely with the pipe 11 because all the tubes of 12 to 15 are within the pipe 11.

Each of the tubes 12 to 15 has an associated set of pickup electrodes 12b to 15b and a final set of pickup electrodes 17 are arranged within the pipe 11, between the tube of largest radius 12 and the transmission electrodes 16.

Figure 3:
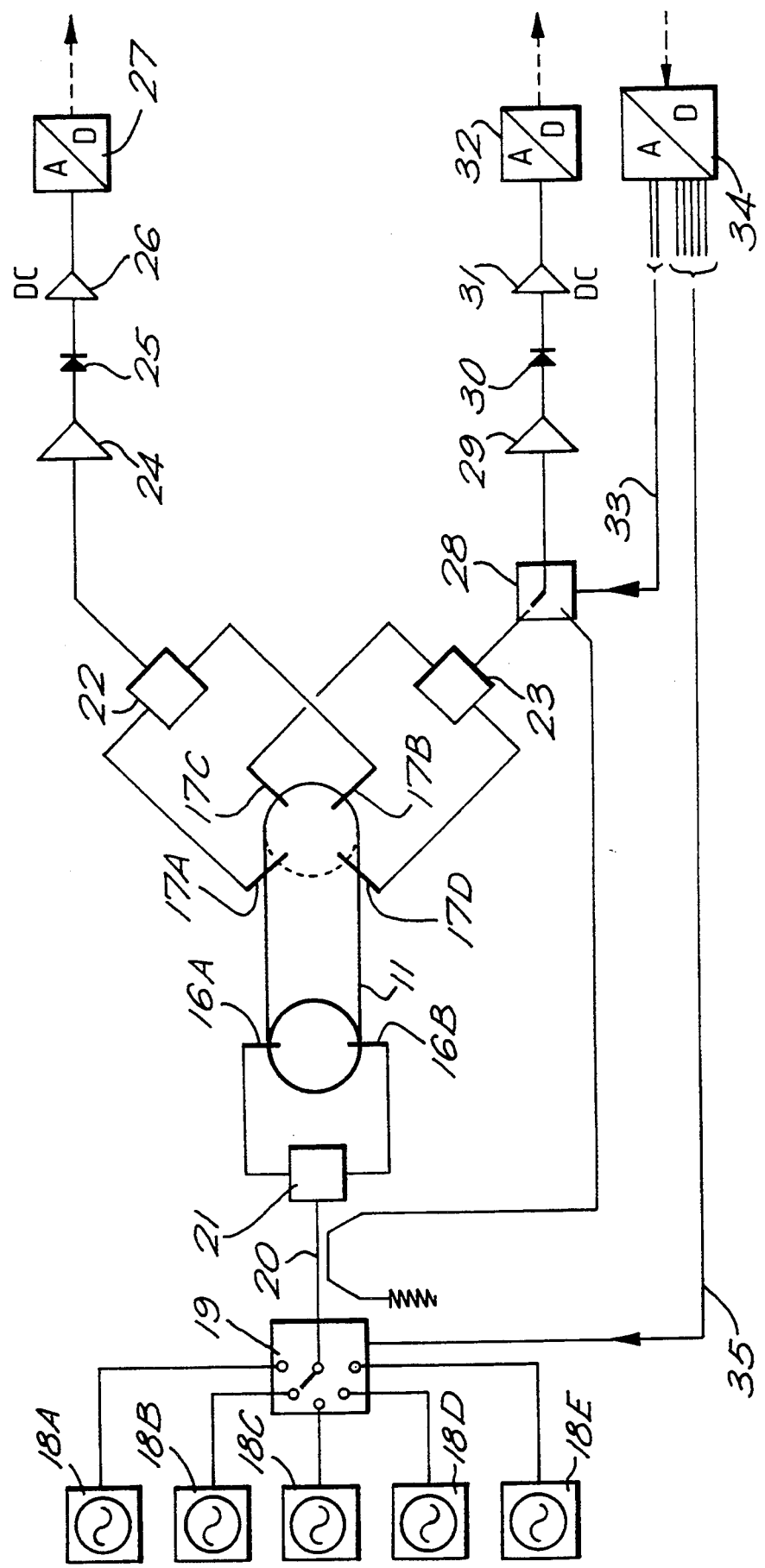
FIG. 3 shows the electronics used in the system of FIG. 2.

The sets of vanes 12a to 15a divide up the annular regions between the wall of the pipe 11 and the outer surfaces of the tubes 12 to 15, into small enough portions that the cut-off frequency for transmission through these regions is very high, and also provide electrical contact between the pipe 11 and tubes 12 to 15. Although it is not simple to calculate cut off frequencies for irregularly shaped areas like those defined by the vanes, it is possible, by dividing each region into small enough segments, to ensure that their cut-off frequencies are so high that they will not propagate the radiation used by the system under any circumstances. Referring to FIG. 3, the structure of the electrode sets 12b to 15b, 16 and 17, and their associated electronics, are shown.

The transmission electrodes 16 comprise two electrodes 16a and 16b situated diametrically opposite one another on the pipe 11. All of the electrodes are insulated from contact with the conductive pipe 11 and tubes 12, 13, 14 and 15 by coaxial insulators. These insulating techniques are very well known and, for simplicity, are not illustrated in the figures.

To provide a variable frequency input signal to the transmission electrodes 16a and 16b, a plurality of crystal oscillators 18a to 18e are used, oscillating at frequencies of 0.6, 0.9, 1.2, 1.45 and 1.7 GHz respectively. All of the oscillators 18a to 18e are linked to a single pole multi-position switch 19 which can connect any of them to the output of the switch 19. Thus any one, and only one, of the signals from the crystal oscillators 18a to 18e can be produced as the output of the switch 19. This output signal passes through a coupler 20 to a 180° coupler 21. The two outputs from the 180° coupler 21 are connected to the two transmission electrodes 16a and 16b. As a result, the signals at the two transmission electrodes 16a and 16b are 180° out of phase versions of the signal generated by one of the crystal oscillators 18A to 18E, and this signal will be transmitted into the pipe 11 in the TE$_{11}$ mode.

Each of the sets of receiver electrodes 12b to 15b and 17 comprise four electrodes arranged 90° apart around the circumference of their respective pipe or tube. Their angular position relative to the transmission electrodes 16 around the circumference of the pipe is not significant. In FIG. 3, only the set of electrodes 17a, 17b, 17c and 17d are shown with their associated electronics, but all of the other sets of receiver electrodes 12b to 15b are the same, and will have similar associated electronics.

The four electrodes 17a to 17d are arranged 90° apart around the circumference of the pipe 11 so as to form two diametrically opposed pairs 17a, 17b and 17c, 17d. Each pair of receiver electrodes 17a, 17b and 17c, 17d are connected to two inputs of a respective 180° coupler 22, 23. The outputs from the 180° couplers 22 and 23 will comprise all the signals which are out of phase at the two electrodes of their respective pair 17a, 17b and 17c, 17d. All electrical signals which are in phase at the two electrodes of each pair will cancel. The signal from the 180° coupler 22 passes through an amplifier 24 and is converted to a d.c. voltage by a diode 25 and is amplified by a further amplifier 26 and is then digitized by analog to digital converter 27 which converts it into a digital optical signal in an optical fiber, leading to a controlling computer (not shown).

The output from the 180° coupler 23 passes through a switch 28, which is also supplied with the output from the coupler 20, and the output from this switch then passes through an amplifier 29, diode 30, amplifier 31 and analog to digital converter 32, similarly to the output signal from the 180° coupler 22. The switch 28 is controlled by signals on a line 33 from the computer via a digital to analog converter 34, and can be switched to provide the computer with a sample, either of the signal across the electrode pair 17c, 17d, or a sample from the coupler 20 of the signal being transmitted by the transmitter electrodes 16a, 16b. Only the set of electrodes 17 will have a switch 28 connected in this way. This switch will be omitted on all the other sets of receive electrodes 12b to 15b.

The position of the switch 19 is controlled by signals from the computer along the line 35.

In operation, the computer connects each of oscillators 18a to 18e in turn to the transmit electrodes 16a and 16b using the switch 19 and checks the precise frequencies being generated by the oscillators 18a to 18e using the switch 28. At each transmit frequency, the computer looks at the received signals in all the sets of receive electrodes 17, 12b, 13b, 14b and 15b, and measures the intensity of the microwave radiation received at each of the sets of receiver electrodes, and the relative time delay between transmitted signals and the received signals at the different sets of receiving electrodes.

By measuring which frequencies and microwave radiation will propagate along which of the tubes 12 to 15, the average dielectric constant of the material within the pipe at a range of frequencies can be calculated. Since the conductivity of the pipe 11 and tubes 12 to 15 is known, the changes in the microwave energy in the pipe when it is propagating can be used to calculate the absorption of the material within the pipe 11 at these frequencies, and the phase insertion and time delays can be measured.

The dielectric constant and absorption coefficient of a material form its complex permitivity, and the ratio between them is often referred to as the loss tangent. Having worked out both the dielectric constant and the absorption coefficient, the complex permitivity and loss tangent can be found if desired.

The complex permitivity, or loss tangent, of water is variable with frequency and, as a result, by calculating the dielectric properties of material within the pipe 11 at two or more different frequencies, the relative quantities of gas, water and oil within the pipe 11 can be calculated.

The effects of inhomogeneity of the oil, water and gas fluid mixture within the tube 11 have not been discussed above. Although the measurements of dielectric properties produced will be averages for all material within the pipe 11 and tubes 12, 13, 14 and 15, between the respective transmit and receive electrodes used, there is a problem that inhomogeneity of the fluid mixture will cause mode conversion. That is, inhomogeneity in the fluids within the pipe 11 will cause radiation in the $TE_{11}$ mode to be converted into other modes. This problem can be avoided by only using as a basis of calculation, measurements of dielectric properties based on radiation at frequencies between the $TE_{11}$ mode and $TM_{01}$ mode for the tube that the electrodes are in. Because the $TE_{11}$ mode is the lowest frequency mode which can propagate in a tube, and the $TM_{01}$ mode is the next lowest frequency mode which can propagate in the tube, where frequencies between the frequencies of these two modes are used, there is no possibility of mode conversion because none of the modes other than the $TE_{11}$ mode can propagate. By employing the $TE_{11}$ and $TM_{01}$ cut off frequencies, the cut off frequencies can be easily be distinguished. As a result, measurements made between these frequencies can be relied on, and due to the use of a plurality of tubes with different radii, there will always be plenty of data available at these frequencies in at least one of the tubes.

The receive electrodes are arranged as two pairs of diametrically opposed electrodes with each pair being 90° apart from the other pair. The receive electrodes will pick up all modes and can be used to sense the relative energies in different modes at frequencies allowing multiple modes to propagate. These relative energies can be compared and, by doing this, the degree of inhomogeneity of the fluid within the pipe 11 can be calculated.

This system is particularly suitable for under sea use for measuring the oil and gas content of crude oil.

If a more accurate measurement of cut off frequency/is required, this can be provided by adding frequency mixing systems to generate a sweepable frequency input for the transmit electrodes, rather than an input variable only in steps.

Other numbers of tubes than those shown could of course be used.

The systems described will only measure the proportions of oil, water and gas in the flow. In order to measure the absolute amounts, means to measure the rate of flow of the fluid in the pipe will be needed in addition.

I claim:

1. An apparatus for measuring the relative proportions of gas, oil and water in a conductive pipe comprising:

at least one open-ended, conductive tube having a radius different from the conductive pipe, disposed within the conductive pipe;

microwave transmission means for transmitting microwave signals along the conductive pipe and at least one tube at a plurality of frequencies, wherein the conductive pipe and the at least one conductive tube each act as waveguides for the microwave signals;

at least two microwave receiving means disposed at separate positions in the conductive pipe and at least one conductive tube, the positions being at locations having different respective radii, and being spaced apart along the conductive pipe and at least one conductive tube, for receiving the microwave signals transmitted by said transmission means; and determining means for determining the relative proportions of gas, water and oil in the conductive pipe by comparing the transmitted and received signals.

2. The apparatus as claimed in claim 1, wherein the at least one conductive tube comprises a plurality of conductive tubes having different respective radii from each other and from the conductive pipe, the plurality of conductive tubes being arranged in order of descending radius, with a conductive tube having a relatively largest radius being disposed nearest to the microwave transmission means.

3. The apparatus as claimed in claim 2, wherein each of the plurality of conductive tubes, except for the conductive tube of relatively largest radius, has one end disposed within a conductive tube of a relatively larger radius.

4. The apparatus as claimed in claim 1, wherein the microwave receiving means are disposed within the conductive pipe between the microwave transmission means and the plurality of conductive tubes, and within each conductive tube.

5. The apparatus as claimed in claim 1 wherein the microwave transmission means transmits microwaves along the conductive pipe at a plurality of discrete frequencies.

6. The apparatus as claimed in claim 1, wherein the microwave transmission means transmits microwaves along the conductive pipe at a continuous range of frequencies.

* * * * *